United States Patent [19]
Dobak, III et al.

[11] Patent Number: 5,820,542
[45] Date of Patent: Oct. 13, 1998

[54] MODIFIED CIRCULATORY ASSIST DEVICE

[75] Inventors: John D. Dobak, III, Del Mar; Kambiz Ghaerzadeh, San Diego, both of Calif.

[73] Assignee: Momentum Medical, Inc., San Jose, Calif.

[21] Appl. No.: 891,545

[22] Filed: Jul. 11, 1997

Related U.S. Application Data

[63] Continuation-in-part of Ser. No. 740,657, Oct. 31, 1996.
[51] Int. Cl.⁶ .................................................. A61B 19/00
[52] U.S. Cl. .............................................................. 600/16
[58] Field of Search ........................... 600/16–18; 623/3; 606/192, 194, 198; 604/4–6, 65–67, 150–152, 891.1

[56] References Cited

U.S. PATENT DOCUMENTS

| | | | |
|---|---|---|---|
| 4,990,139 | 2/1991 | Jang | 606/192 X |
| 5,139,517 | 8/1992 | Corral | 623/3 |
| 5,176,619 | 1/1993 | Segalowitz | 600/18 |
| 5,213,576 | 5/1993 | Abiuso et al. | 606/192 X |
| 5,308,319 | 5/1994 | Ide et al. | 600/18 |
| 5,409,444 | 4/1995 | Kensey et al. | 600/18 |
| 5,453,076 | 9/1995 | Kiyota et al. | 600/18 |
| 5,569,184 | 10/1996 | Crocker et al. | 604/53 |

OTHER PUBLICATIONS

Frazier, O.H.; *Clinical Use of the Hemopump*; pp. 146–152; date and place of publication unknown.
Verkerke, Bart; *The PUCA Pump: A Left Ventricular Assist Device*; pp. 365–368; 1993; Artificial Organs, vol. 17, No. 5.
Abstracts by various authors; pp. 469, 551, 559; 1993; Artificial Organs, vol. 17, No. 6.
Abstract of U.S. Pat. No. 4,407,271 to Schiff, P.; Apparatus for left Heart Assist; Oct. 4, 1983; patent no available.
Abstract of U.S. Pat. No. 4,522,195 to Schiff, P.; Apparatus for Left Heart Assist; Jun. 11, 1985; patent not available.
Abstract of U.S. Pat. No. 4,685,446 to Choy, D.; Method for Using a Ventricular Assist Device; Aug. 11, 1987; patent not available.
Abstract of U.S. Pat. No. 4,771,765 to Choy, D.; Heart Assist Device and Method of Use; Sep. 20, 1988; patent not available.
Abstract of U.S. Pat. No. 4,861,330 to Voss, G.; Cardiac Assist Device and Method; Aug. 29, 1989; patent not available.
Abstract of U.S. Pat. No. 4,902,273 to Choy, D.; Heart Assist Device; Feb. 20, 1990; patent not available.
Kabei, N.; *Right Ventricular Balloon Pumping*; abstract; Oct., 1985; Life Support Systems.
Moulopoulis, S.; *Intraventricular Plus Intra–aortic Balloon Pumping During Intractable Cardiac Arrest*; abstract; Nov., 1989; Circulation.
Stamatelopoulos, S; *Left Intraventricular Balloon Pump Optimization During Intractable Cardiac Arrest*; abstract; Jul. 1996; International Journal of Artificial Organs.

*Primary Examiner*—Jeffrey R. Jastrzab
*Attorney, Agent, or Firm*—Gerald W. Spinks

[57] ABSTRACT

A circulatory assist device, having a housing and a pumping membrane, with a control chamber and a pumping chamber. The device is mounted on a catheter, collapsed to a sufficiently small diameter to allow insertion into the vascular system of a patient. An expansion mechanism in the device, such as a stent, can be expanded to hold the housing in an expanded substantially rigid state, while control fluid is pumped into and evacuated from the control chamber to repeatedly deflect the pumping membrane. At least one opening is formed in the device, to allow vascular fluid to enter and exit the pumping chamber as the pumping membrane deflects. Introduction and evacuation of control fluid can be synchronized with the heart cycle of the patient. After use, the housing is contracted to a smaller diameter to allow withdrawal from the vascular system.

17 Claims, 9 Drawing Sheets

MODIFIED CIRCULATORY ASSIST DEVICE

CROSS REFERENCE TO RELATED APPLICATIONS

This is a continuation-in-part patent application of co-pending U.S. patent application Ser. No. 08/740,657, filed on Oct. 31, 1996, and entitled "Intravascular Circulatory Assist Device".

BACKGROUND OF THE INVENTION

This invention is in the field of devices used to augment or replace the pumping capacity or other flow capabilities of a vascular system, such as the cardiovascular system. In particular, the present invention is in the field of devices which can be inserted percutaneously into a vascular system to augment the pumping capabilities of the system.

There are a number of conditions which can seriously impair the ability of a vascular system to maintain its required fluid flow rate. Different vascular systems are subject to different disorders which can impair the flow of vascular fluid. In particular, in the cardiovascular system, the heart is in some circumstances unable to maintain adequate circulation of blood. Some of the conditions which can impair the ability of the heart to maintain the flow rate are myocardial infarction, physical trauma to the heart, cardiomyopathy, and infectious disease. The heart may fibrillate, or it may stop beating altogether, known as asystole, with either condition resulting in the inability to provide any flow. In addition, the performance of some surgical procedures, such as coronary artery bypass, may require that the heart be artificially arrested for the duration of the procedure.

There are also conditions in which blood flow to a single organ may be reduced. In such a case, it may be desirable to selectively perfuse the organ, applying a higher pressure than that which can be provided by the circulatory system. An example of such a condition is atherosclerotic disease of the coronary arteries. In such a condition, the lumens of one or more coronary arteries are restricted by atheroma or atherosclerotic plaque. This results in a reduction in the blood flow rate to the heart muscle distal to the restricted section of artery. This reduction in blood flow rate can result in damage to the heart muscle, or to the tissues of any other organ which is so affected, caused by a reduction of the oxygen supply to the organ. Such a condition can be alleviated, at least temporarily, by increasing the blood pressure in the artery proximal to the restriction, to increase perfusion of the organ. Theoretically, an increase in the blood pressure provided by the circulatory system can be achieved by the administration of heart stimulants, or by the administration of blood transfusions. Unfortunately, these therapies also increase the work load on the heart, thereby increasing the oxygen demand of the heart, resulting in a cancellation of the effect of the additional oxygen being supplied, where the organ being perfused is the heart. The increased demand can even exceed the additional oxygen being supplied.

Regardless of the exact nature of the reduction of flow, whether a reduction of cardiac output, a localized circulatory reduction, or a complete circulatory failure, it is desirable to be able to provide circulation of the blood with an artificial device. Such devices are commonly called circulatory assist devices. Heart failure, fibrillation, and asystole often require emergency care, because of the limited time during which remedial actions must be taken in order to be effective. In order for a circulatory assist device to be useful in the emergency care situation, the device must be quickly and easily insertable to the desired vascular location where the circulatory assistance is most effectively applied. Percutaneous application is the most advantageous procedure, because physical trauma to the patient is limited in such a procedure, and because emergency medical personnel are familiar with percutaneous insertion of various types of devices.

It is also highly desirable for a circulatory assist device to possess several other attributes. It should be capable of providing a flow rate of at least 2.5 liters per minute, while maintaining an average arterial pressure of 90 mm of Hg. It is preferable that this flow be pulsatile, rather than continuous. Natural blood flow is pulsatile, and data shows that recovery is better when flow is pulsatile. The device should also be able to pump in synchrony with various points of the heart cycle or ECG, should a patient have some baseline function.

The outside diameter of the device and its delivery catheter should be limited to no greater than 4 mm. This will minimize any damage to the blood vessel through which it passes. Further, this limited diameter will limit ischemia of the tissues distal of the insertion site during long periods of use. The circulatory assist device should have as few moving parts as possible, in order to minimize the chance of mechanical failure, and to limit the fabrication cost. The device should also be constructed so as to inflict as little damage as possible to blood cells. Finally, the device should be constructed so as to minimize the opportunity for coagulation within the device.

It is the object of the present invention to provide a circulatory assist device which can be mounted to a catheter for percutaneous insertion into the vascular system and for advancement to the treatment area, where increased flow is to be provided, with the diameter of the device being small enough to cause minimal trauma to the vascular system. It is a further object of the present invention to provide the circulatory assist device with a means for expanding to an operating volume, once located in the treatment area, with the operating volume being sufficiently large to provide an adequate flow rate of vascular fluid. It is a still further object of the present invention to provide the circulatory assist device with a pumping mechanism which has a minimum of moving parts, and which will cause minimal trauma to the cells of the vascular fluid.

BRIEF SUMMARY OF THE INVENTION

The present invention comprises a circulatory assist device, which, by way of example, incorporates an expandable housing, which can incorporate an expansion mechanism, mounted to a catheter. The housing can incorporate an inflatable membrane, or it can be simply a relatively open fluid container, open on one end, or even tubular. An inner pumping membrane is mounted within the expansion mechanism and housing. The pumping membrane can be an enclosure, encompassing either a pumping chamber or a control chamber, or it can constitute just one wall of a control chamber. Where the pumping membrane is an enclosure encompassing a pumping chamber or a control chamber, vascular fluid is moved by expansion and collapse of the pumping membrane. Where the pumping membrane constitutes one wall of a control chamber, vascular fluid is moved by inward and outward flexing of the pumping membrane.

Importantly, the expanded housing of the present invention provides an enclosure which will not expand further when the control chamber is expanded, to provide a space within which efficient pumping can take place. It is known to insert a balloon into the thoracic aorta and repeatedly expand and collapse the balloon to augment blood flow. It has been noted, however, that if a balloon is expanded and contracted within a pliable enclosure, such as an artery or a heart chamber, the artery or heart chamber will expand with each expansion of the balloon. This expansion of the "pumping enclosure" prevents efficient expulsion of the vascular fluid from the space between the balloon and the artery wall. Therefore, it is significant that the present invention incorporates a housing which will not further expand when the control chamber is pressurized. It has been found that this can increase the pumping output by a factor of two (2), or more.

If the pumping membrane of the present invention is designed to encompass a pumping chamber, it has at least one port through its wall, with the construction of the circulatory assist device being such that the port can be exposed to vascular fluid. If the pumping membrane is designed to encompass a control chamber, it encompasses at least one control fluid port through the catheter wall, with the construction of the circulatory assist device being such that control fluid can be delivered to the control fluid port to effect expansion and collapse of the pumping membrane. In either case, the pumping membrane is expanded and collapsed to cause vascular fluid, such as blood, to flow through the circulatory assist device as the pumping membrane expands and collapses.

If the pumping membrane is designed to form one wall of a control chamber, it has one side which can be exposed to vascular fluid. The other side of the pumping membrane is exposed to at least one control fluid port in the catheter wall, with the construction of the circulatory assist device being such that control fluid can be delivered to the control fluid port to effect inward and outward flexing of the pumping membrane. In this design, the pumping membrane is flexed inwardly and outwardly to cause vascular fluid, such as blood, to flow through the circulatory assist device as the pumping membrane flexes.

A single vascular fluid port can be provided in the circulatory assist device to allow vascular fluid to flow into and out of the device through the same port. This single port reciprocating type of flow can be used where the device is positioned within the left ventricle of the heart, for instance, making use of the unidirectional flow characteristics of the mitral valve and the aortic valve. Alternatively, instead of using a single port, two or more ports can be used to control the direction of flow of the fluid. For instance, the ports can be fitted with one way valves to cause the vascular fluid to enter the circulatory assist device through the appropriate port, and to exit the circulatory assist device through the appropriate port, flowing in the desired direction. Further, a flow through type of housing can be utilized, being essentially open on both ends. Either the multiple-port or the flow-through unidirectional type of flow can be used where the device is positioned within the aorta. Additionally, in the multiple port type of device, either the inlet port or the outlet port can be fitted with an external tube to draw fluid from a smaller diameter vessel, or to inject fluid into a smaller diameter vessel. This latter method could be used to provide blood flow into the feeding artery of a selected organ, such as a coronary artery.

Expansion and collapse, or flexing, of the pumping membrane is enabled by first creating a rigid or semi-rigid housing or enclosure having a substantially constant inner space within which the pumping membrane can be repetitively flexed, or expanded and collapsed. This constant inner space between the housing and the pumping membrane can be a control space, if it is used to provide control of the size or shape of the pumping membrane, in which case the other side of the pumping membrane serves as the vascular fluid space. Conversely, the constant inner space within the housing can be a vascular fluid space, in which case the inside of the pumping membrane encompasses a control space, which is used to provide control of the size of the pumping membrane.

First, the housing and the pumping membrane are introduced percutaneously into the vascular system while maintained at a first, relatively small, diameter. The housing and the pumping membrane, still in a collapsed condition, are advanced to the treatment area, such as the left ventricle of the heart. Then, the housing is expanded to a selected, relatively larger, diameter, the size of which depends upon the size of the treatment area. Along with the housing, an expansion mechanism is expanded to this selected larger diameter. The expansion mechanism and the housing constitute a rigid or semi-rigid enclosure for the control space.

The expansion mechanism is designed to maintain the larger diameter until it is reshaped to a smaller diameter for eventual withdrawal from the vascular system. The expansion mechanism can either provide the expansion force itself, or it can be expanded by fluid pressure or other forces. The expansion mechanism is located near the housing; it can be positioned inside the housing, or outside the housing, or it can be incorporated in the wall of the housing. The expansion mechanism can also be attached to the housing, for instance if it is positioned outside the housing. It can be an expandable stent, which is expanded by fluid pressure inside the housing, if the housing incorporates an inflatable outer membrane. This hydraulically expandable type of stent requires a protective membrane outside the outer membrane, which can be pressurized to return the stent to its smaller diameter. Alternatively, the expandable stent can be made of a thermally expandable material, such as a nickel titanium alloy. Such a thermally expandable stent can be expanded to the larger diameter by being exposed to a first temperature, such as a relatively higher temperature, and returned to the smaller diameter by being exposed to a second temperature, such as a relatively lower temperature. Exposure of the thermally expandable stent to the vascular fluid can cause it to expand, or a control fluid at the appropriate temperature can be used for this purpose. In either case, a control fluid at the desired second temperature can be used to return the thermally expandable stent to the smaller diameter.

The expansion mechanism can also take other forms. A self-expanding element can be used, such as an outwardly biased cylindrical cage or a plurality of outwardly biased flexible prongs. The self-expanding element can be retained at a smaller diameter by a retention sheath, until positioned in the treatment area. Then, the self-expanding element can be expelled from the retention sheath to allow the self-expanding element to expand to a larger diameter, thereby expanding the housing along with it. The outward bias of the self-expanding element would maintain the housing at the larger diameter, functioning as the rigid or semi-rigid enclosure, to maintain the space within which the inner membrane operates.

Further, the expansion mechanism can take the form of a helical spring which has a larger diameter associated with a shorter length, and which has a smaller diameter associated with a longer length. The spring can be biased toward either the shorter length or the longer length. Selectively changing the length of the spring transforms its diameter accordingly.

If the spring is biased toward the shorter length, it can be held under tension until positioned in the treatment area, at which time the tension can be released, allowing the spring to transform to the larger diameter. Conversely, if the spring is biased toward the longer length, it can be placed under compression once in the treatment area, transforming the spring to the shorter length and the larger diameter. In either case, reversing the process transforms the spring to the smaller diameter for withdrawal from the vascular system, once the pumping has been completed.

Regardless of the type of expansion mechanism used, a constant inner space is created inside the housing, between the housing and the pumping membrane. Control fluid can be repeatedly pumped into, and evacuated from, this constant inner space, where the constant space is utilized as a control space. When control fluid is pumped into the control space, the pumping membrane collapses, or flexes outwardly, expelling any vascular fluid which may be inside the device. When the control fluid is evacuated from the control space, the pumping membrane expands, or flexes inwardly, drawing in vascular fluid. Repetition of this process provides the necessary flow of vascular fluid.

Alternatively, where the pumping membrane encompasses a control chamber, control fluid can be repeatedly pumped into, and evacuated from, the space within the pumping membrane. When control fluid is pumped into the control space, the pumping membrane expands, expelling any vascular fluid which may be in the constant inner space between the housing and the pumping membrane. When the control fluid is evacuated from the control space, the pumping membrane collapses, drawing vascular fluid into the constant inner space between the housing and the pumping membrane. Repetition of this process provides the necessary flow of vascular fluid.

If the heart has some baseline, albeit diminished, pumping activity, the pumping of fluid into the control space must be timed with the cardiac cycle. If the pump is placed in the aorta, then the pumping should be synchronized with diastole. If it is placed in the ventricle, it should be synchronized with systole.

The novel features of this invention, as well as the invention itself, will be best understood from the attached drawings, taken along with the following description, in which similar reference characters refer to similar parts, and in which:

DETAILED DESCRIPTION OF THE INVENTION

The present invention is a circulatory assist device which consists primarily of a pumping mechanism utilizing a housing and a pumping membrane mounted on a catheter. The housing, which can be equipped with an expansion mechanism, provides an enclosure within which the pumping membrane can flex, or expand and collapse, to take in and expel a vascular fluid. The space between the pumping membrane and the housing can be repeatedly evacuated and then pressurized with a control fluid, to flex or expand and collapse the pumping membrane. Alternatively, a space enclosed within the pumping membrane can be repeatedly evacuated and then pressurized with a control fluid, to expand and collapse the pumping membrane.

Figure 1:
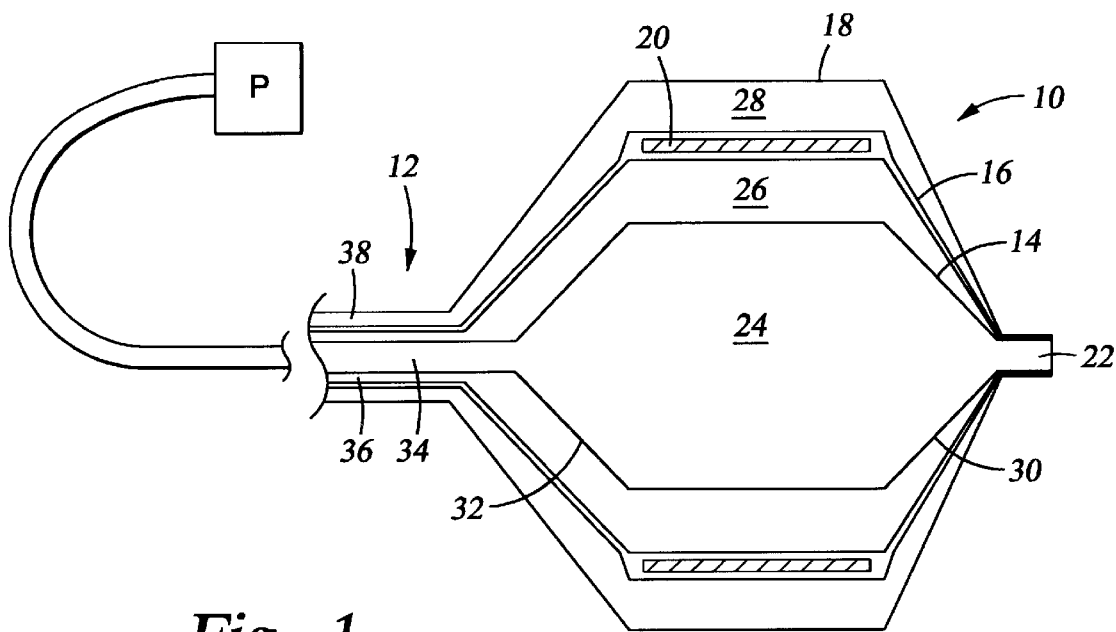
FIG. 1 is a section view of a first embodiment of the apparatus of the present invention.

As seen in the embodiment shown in FIG. 1, the circulatory assist device (CAD) 10 of the present invention is mounted on a catheter 12. The CAD 10 includes a flexible inner pumping membrane 14, and a flexible housing 16 surrounding the pumping membrane 14. Depending upon the means by which the expansion of the CAD 10 is achieved, the CAD 10 can also be fitted with a flexible protective membrane 18, surrounding the housing 16. In some embodiments, a protective membrane 18 is not required. The housing 16 and the membranes 14, 18 can be made of a flexible material which can expand up to a desired size, or diameter, after which the material essentially does not expand further, even if the pressure inside the housing or membrane is increased further. Such materials, and the processes used in their fabrication, are widely used in the manufacture of balloons for angioplasty.

An expansion mechanism, such as a substantially cylindrical expandable stent 20, can be mounted in the CAD 10, near the housing 16. The stent 20 can be incorporated in the wall of the housing 16, or the housing 16 could consist of two laminated membranes, with the stent 20 captured therebetween. Alternatively, as will be illustrated below, the stent 20, or another similar expansion mechanism, could be located inside the housing 16, or outside the housing 16. Various other embodiments of the expansion mechanism can be used in place of the stent 20, but the stent 20 will generally be described herein, with the understanding that other embodiments could also be used. In any case, the expansion mechanism is positioned relative to, or attached to, the housing 16 in such a way that the housing 16 will expand with the expansion mechanism.

The stent 20 is an expandable, substantially cylindrical, lattice of elongated elements of plastic or metal. It can be similar to cardiovascular stents known in the art. The stent 20 is assembled in the CAD 10 while at a smaller diameter, substantially the diameter of the catheter 12. When the CAD 10 is positioned in the treatment area, fluid pressure can be introduced inside the stent 20 and the housing 16, to expand the stent 20 to a larger diameter. When the internal pressure is released, the stent 20 will retain its larger diameter, until it is eventually compressed by the application of fluid pressure to the outer surface of the stent 20. In some other embodiments, the expansion mechanism itself provides the expanding force, such as stents made of a nickel-titanium alloy, such as nitinol, which expands upon exposure to a higher temperature. Other stents can be mechanically biased toward a larger or smaller diameter, and physically manipulated to achieve the desired diameter. In all embodiments, once expanded, the purpose of the expansion mechanism is to hold the housing 16 in the expanded state.

FIG. 1 shows the CAD 10 in its expanded state, wherein the housing 16, the membranes 14, 18, and the stent 20 are all expanded to a diameter which is relatively larger than the diameter of the catheter 12. This expanded diameter provides sufficient room for adequate pumping capacity. For use in the cardiovascular system of an adult patient, an expanded diameter of 35 mm. might be used. The housing 16, the membranes 14, 18, and the stent 20 are also collapsible to a relatively smaller diameter, in the range of 2.5 to 4 mm., at which the CAD 10 is essentially the same diameter as the catheter 12. This contracted diameter makes the CAD 10 small enough to be easily inserted percutaneously and advanced through the vascular system of the patient.

A port 22 for the flow of blood or other vascular fluid is formed in the distal end of the pumping membrane 14, extending through the housing 16 and the protective membrane 18. When the CAD 10 is positioned within a vascular system, such as the cardiovascular system, of a patient, the CAD 10 is positioned so that the port 22 is exposed to the blood in the system, at the treatment area, where circulatory assist is required. For example, depending upon the particular embodiment of the invention in use, the location of the CAD 10 could be in the left ventricle of the heart, or it could be in the aortic arch.

When the pumping membrane 14 is in the expanded state, a pumping chamber 24 within the pumping membrane 14 is expanded to its largest volume. The expansion of the pumping chamber 24 draws in the vascular fluid through the port 22. Subsequent collapse of the pumping chamber 24 expels the vascular fluid through the port 22. The size of the pumping chamber 24 can be designed to achieve the desired flow rate, given a selected pulse rate. For instance, if the CAD 10 is to be used in the cardiovascular system, it has been found that pulsatile flow at the frequency of the heartbeat is most beneficial. A pulse rate of 100 cycles per minute would be reasonable. In the cardiovascular system, it can be desirable to achieve a flow rate of up to 5 liters per minute. Therefore, if these parameters are assumed, the pumping chamber 24 should have a volume of 50 cc. to achieve the desired flow rate.

When the housing 16 is in the expanded state, a control chamber 26 is created between the housing 16 and the pumping membrane 14. This control chamber 26 is repetitively evacuated and pressurized with a control fluid, to achieve the expansion and collapse of the pumping membrane 14. While the housing 16 is held in the expanded state by the stent 20, the total volume enclosed by the housing 16 remains essentially constant, but the volume of the control chamber 26 decreases and increases as the pumping membrane 14 expands and collapses. Pressurization of the control chamber 26 collapses the pumping membrane 14, rather than further expanding the outer balloon 16, because the stent 20 and the housing 16 have been expanded to their greatest possible diameter. Evacuation of the control chamber 26 expands the pumping membrane 14, rather than collapsing the housing 16, because the stent 20 retains its expanded diameter. This requires that the external to internal pressure differential across the housing 16 during evacuation of the control chamber 26 be kept below the pressure differential required to compress the stent 20.

It should be noted that, in the particular embodiment discussed here, with a stent 20 which is expandable and compressible by the application of internal and external fluid pressure, the control chamber 26 is initially pressurized with a control fluid to expand the stent 20 and the housing 16. Once this expansion of the stent 20 has been achieved, the control chamber 26 can then be evacuated and repressurized to achieve the pumping discussed above. When the expansion mechanism is the type which is compressed by external fluid pressure, a second control space 28 is provided between the protective membrane 18 and the housing 16. The second control space 28 can be pressurized with a control fluid to compress the stent 20 and the housing 16 to a smaller diameter, to allow for removal of the CAD 10 from the vascular system. Alternatively, if the thermally expandable stent 20 is used, control fluid at the desired temperature can be introduced into either of the control spaces 26, 28 to control the diameter of the stent 20 and, consequently, the housing 16.

The shape of the pumping membrane 14 shown here is a substantially cylindrical body, with a tapered distal end cone 30 and a tapered proximal end cone 32. The housing 16 and the protective membrane 18 have similar shapes. Other shapes could also be used without departing from the spirit of the present invention.

The catheter 12 has its proximal end connected to a control fluid flow device such as a pump P. The control fluid flow device must be capable of applying a fluid pressure and drawing a vacuum. A syringe could also be used in some of the embodiments. The catheter 12 shown in FIG. 1 is a multi-lumen catheter, but some of the embodiments can be used with single-lumen catheters. A first lumen 34 can be provided in the catheter 12, to allow flow of the vascular fluid into or out of the pumping membrane 14. The first lumen 34 could be used for sampling of the vascular fluid or to direct the vascular fluid from one location to another.

Additional ports (not shown) could be provided proximal to the CAD 10, to allow flow of vascular fluid into or out of the first lumen 34. A second lumen 36 is provided in the catheter 12, to allow the flow of control fluid between the control fluid flow device P and the control chamber 26. The second lumen 36 is used to hydraulically or thermally expand the stent 20 and the housing 16, and to pressurize and evacuate the control chamber 26 for pumping purposes. A third lumen 38 is provided in the catheter 12, to allow the flow of control fluid between the control fluid flow device P and the second control space 28. The third lumen 38 is used to thermally expand the stent 20 to create a pump housing for the pumping membrane 14, or to hydraulically or thermally compress the stent 20 and the housing 16 to a smaller diameter for withdrawal from the vascular system.

Figure 2:
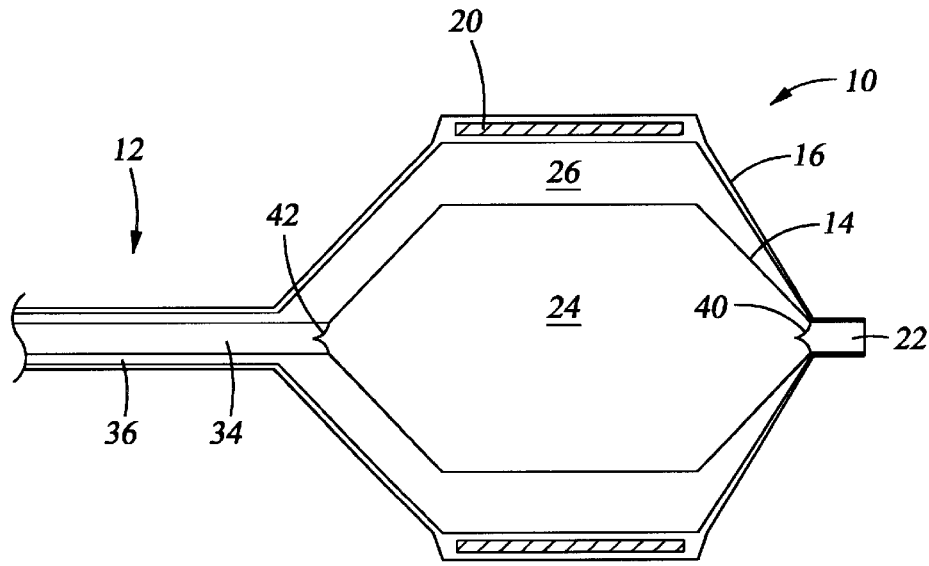
FIG. 2 is a section view of a second embodiment of the apparatus of the present invention, without a protective membrane.

FIG. 2 shows a second embodiment of the present invention with a few variations from the embodiment shown in FIG. 1. The stent 20 used in this embodiment is the thermally expanding stent 20 made of a material such as nitinol. A control fluid at a relatively higher temperature can be introduced into the control chamber 26 through the second lumen 36, to expand the stent 20. Alternatively, the vascular fluid in which the CAD 10 is immersed, such as blood, can be at a sufficiently high temperature to expand the stent 20. Compression of the stent 20 can then be achieved by introducing a control fluid at a relatively lower temperature into the control chamber 26. This embodiment also exhibits a one-way inlet valve 40 in the port 22, and a one-way outlet valve 42 in the first lumen 34, to control the direction of flow of the vascular fluid. The arrangement of the one-way valves 40, 42 would allow the CAD 10 to draw in blood, for instance, at the aortic arch, and direct the flow of blood to a particular artery, to perfuse a selected organ. Other arrangements of one-way valves could be used to control the direction of flow as desired for any particular application.

Figure 3:
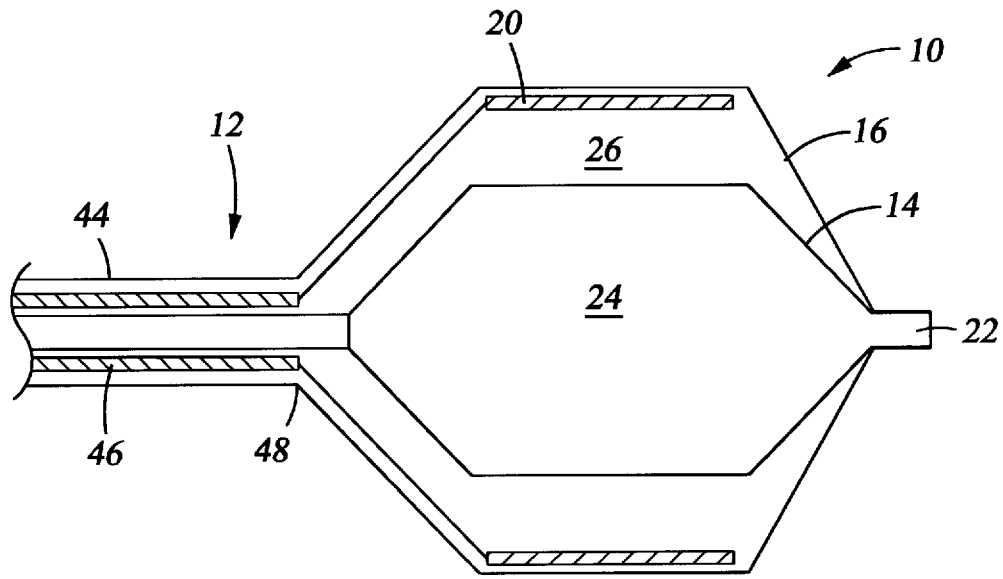
FIG. 3 is a section view of a third embodiment of the apparatus of the present invention, with a first type of self-expanding element.

FIG. 3 shows an embodiment of the CAD 10 which has a self-expanding stent 20. The self-expanding stent 20 shown here is an outwardly biased cage shaped element. The stent 20 can be retained within the retention sheath 44, which is a part of the catheter 12, during insertion of the CAD 10 into the vascular system. Once the CAD 10 is positioned in the treatment area, a positioner 46 can be used to push the stent 20 beyond the distal end 48 of the retention sheath 44, allowing the stent 20 to expand to its larger diameter. Conversely, the positioner 46 can be used to pull the stent 20 back within the retention sheath 44, to reduce the diameter of the CAD 10 for withdrawal from the patient. A protective membrane 18, as shown in FIG. 1, could also be used with the self-expanding stent 20, to allow external pressurization of the stent 20 to hydraulically compress the stent 20 to its smaller diameter. Finally, the thermally expandable stent 20 could be used in the embodiment shown in FIG. 3. Ejection of the thermally expandable stent 20 from the retention sheath 44 would expose the stent 20 to the temperature of the blood, to cause the stent 20 to expand. Control fluid at a lower temperature could then be pumped into the control chamber 26, to return the stent 20 to its smaller diameter.

Figure 4:
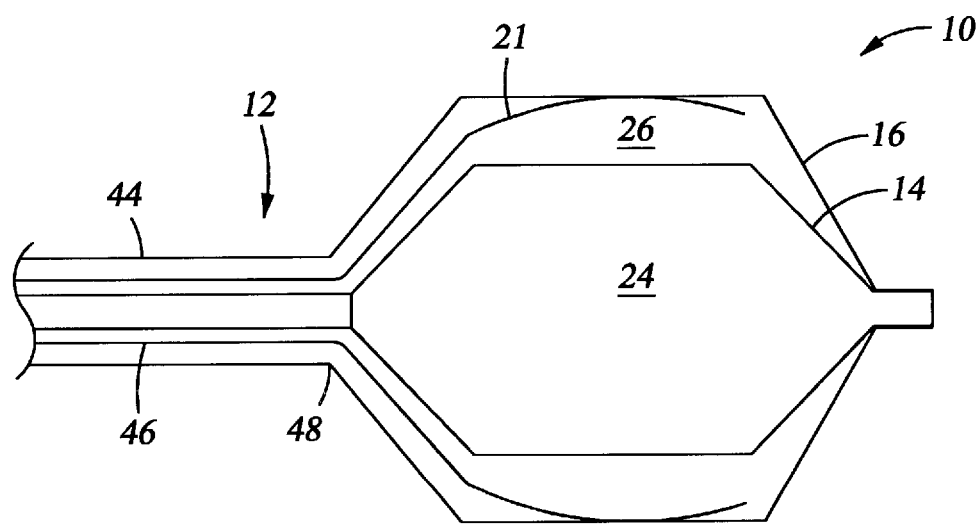
FIG. 4 is a section view of a fourth embodiment of the apparatus of the present invention, with a second type of self-expanding element.

FIG. 4 shows a second type of the self-expanding expansion mechanism in the form of a plurality of flexible, outwardly biased prongs 21. The prongs 21 can be retained within the retention sheath 44, during insertion of the CAD 10 into the vascular system. Once the CAD 10 is positioned in the treatment area, the positioner 46 can be used to push the prongs 21 beyond the distal end 48 of the retention sheath 44, allowing the prongs 21 to expand outwardly, to stretch the housing 16 to its larger diameter. Subsequently, the positioner 46 can be used to pull the prongs 21 back within the retention sheath 44, to reduce the diameter of the CAD 10 for withdrawal from the patient. A protective membrane 18, as shown in FIG. 1, could also be used with the self-expanding prongs 21, to allow pressurization of the second control space 28, to achieve hydraulic compression of the prongs 21, to return the expansion mechanism to its smaller diameter.

Figure 5:
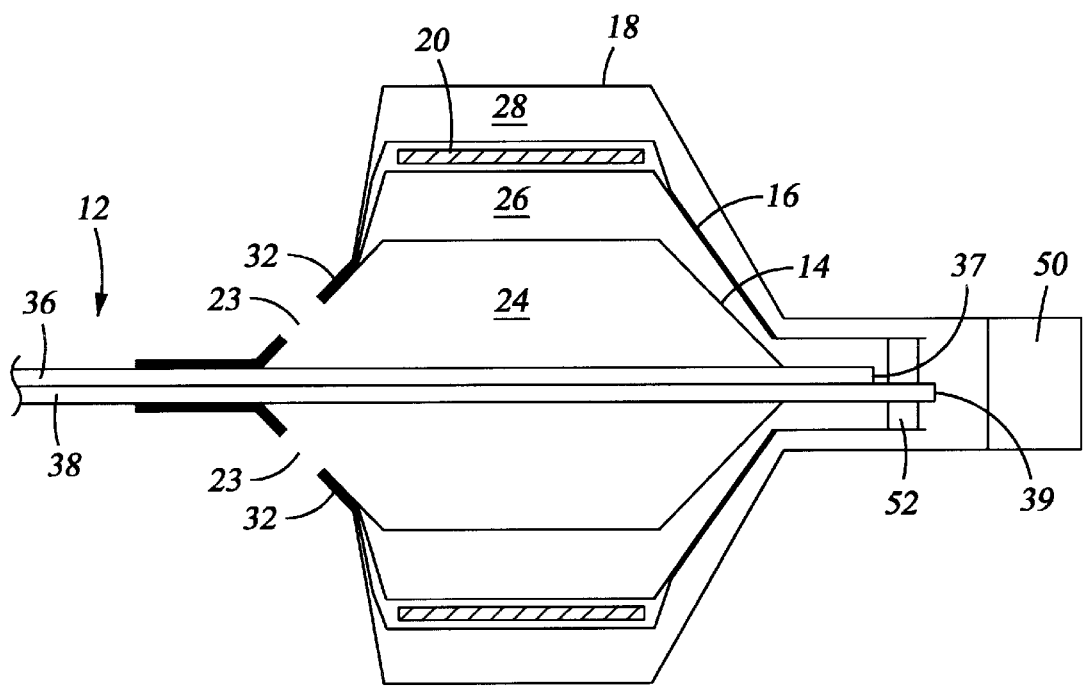
FIG. 5 is a section view of a fifth embodiment of the apparatus of the present invention, with ports in the proximal cone.

FIG. 5 shows an embodiment of the invention in which the vascular fluid enters and exits the pumping chamber 24 through ports 23 located in the proximal cone 32 of the pumping membrane 14. The proximal cones of the housing 16 and the protective membrane 18 are bonded to the proximal cone 32 of the pumping membrane 14. The catheter 12 used with this embodiment is a double-lumen tube. Pressurization and evacuation of the first control chamber 26 are achieved through the first control fluid lumen 36 and the inner control fluid port 37. Pressurization and evacuation of the second control space 28 are achieved through the second control fluid lumen 38 and the outer control fluid port 39. An outer plug 50 seals the distal end of the CAD 10, and an inner plug 52 seals the distal end of the housing 16. This embodiment is particularly useful when it is desirable to direct the flow of vascular fluid proximally. For instance, the CAD 10 can be positioned in the left ventricle, with the ports 23 placed close to, and directed toward, the aortic valve. This would direct the flow of blood through the aortic valve, to assist the action of the ventricle. Depending upon the type of expansion mechanism used with this embodiment, such as the thermally expandable stent 20, the protective membrane 18 may be eliminated.

Figure 6:
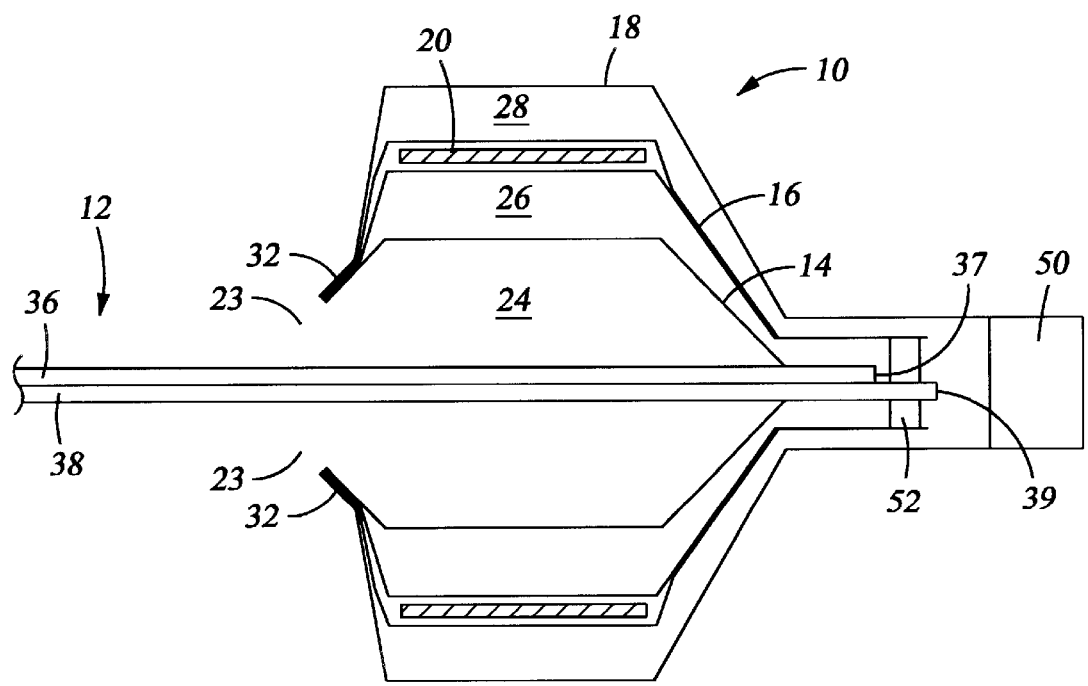
FIG. 6 is a section view of a sixth embodiment of the apparatus of the present invention, with an enlarged port.

FIG. 6 shows another embodiment, which is a variation of the embodiment shown in FIG. 5. In this embodiment, the proximal cones of the housing 16 and the membranes 14, 18 are not attached to the catheter 12, and the port 23 is open all around the catheter 12. This significantly increases the cross-sectional flow area through the port 23.

Figure 7:
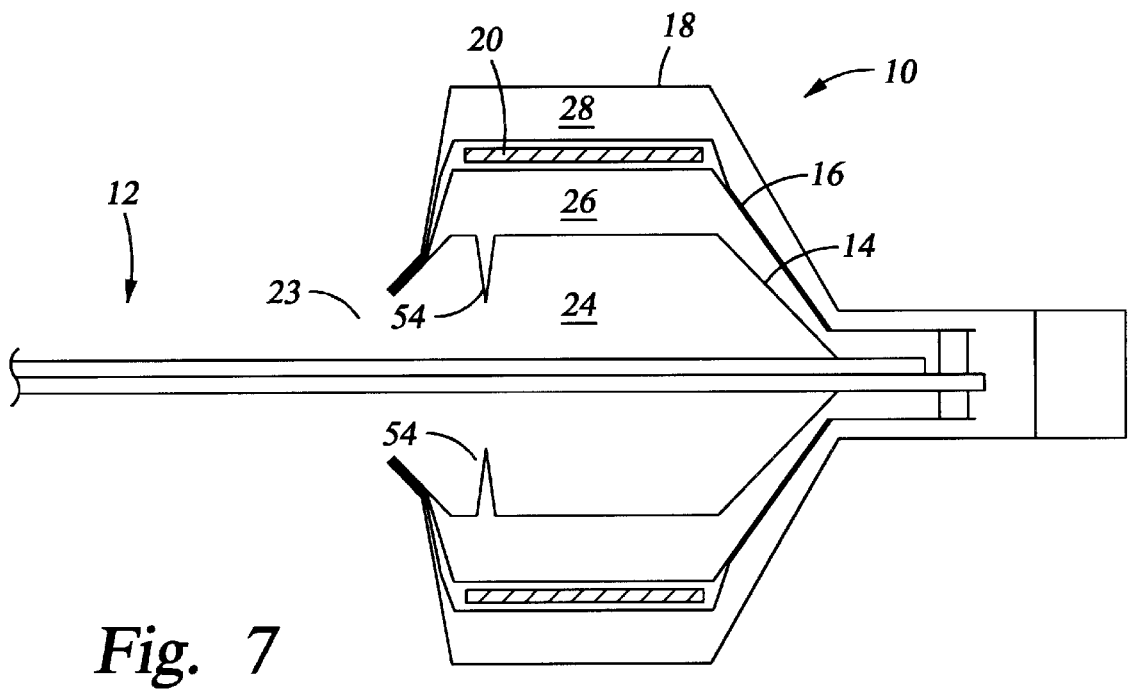
FIG. 7 is a section view of a seventh embodiment of the apparatus of the present invention with a full discharge inner membrane.

In applications where it is necessary to maximize the flow of vascular fluid in each pulse, the embodiments shown in FIGS. 5 and 6 have a disadvantage in that the bonding together of the proximal cones of the housing 16 and the membranes 14, 18 can prevent the complete collapse of the pumping membrane 14. This can be remedied as shown in FIG. 7, where an expansion fold 54 of material is formed in the pumping membrane 14. The expansion fold 54 will fold up when the pumping membrane 14 experiences expansion into the housing 16, and the expansion fold 54 will distend when the pumping membrane 14 collapses, allowing the pumping membrane 14 to fully collapse and completely expel the vascular fluid from the pumping chamber 24.

Figure 8:
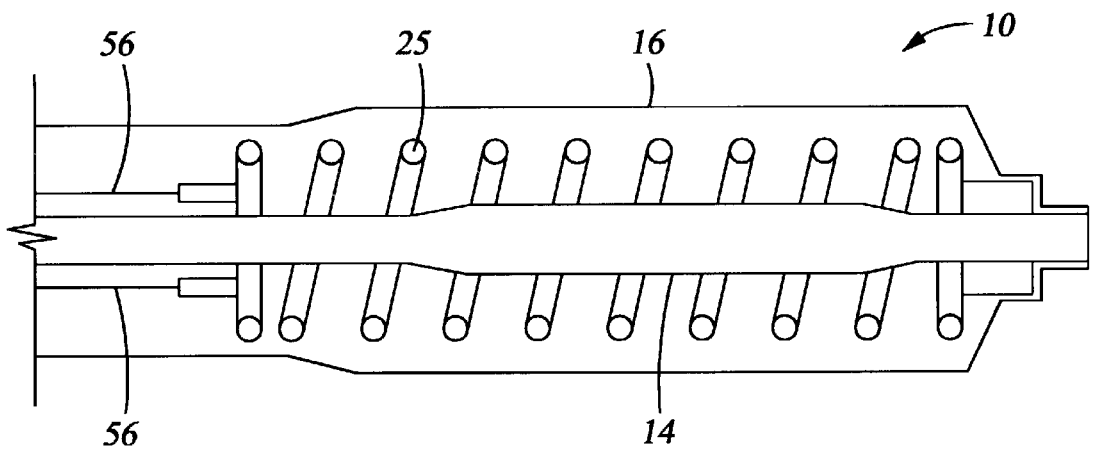
FIG. 8 is a section view of an eighth embodiment of the apparatus of the present invention, with a helical spring expansion mechanism, and with the membranes in the contracted state.
Figure 9:
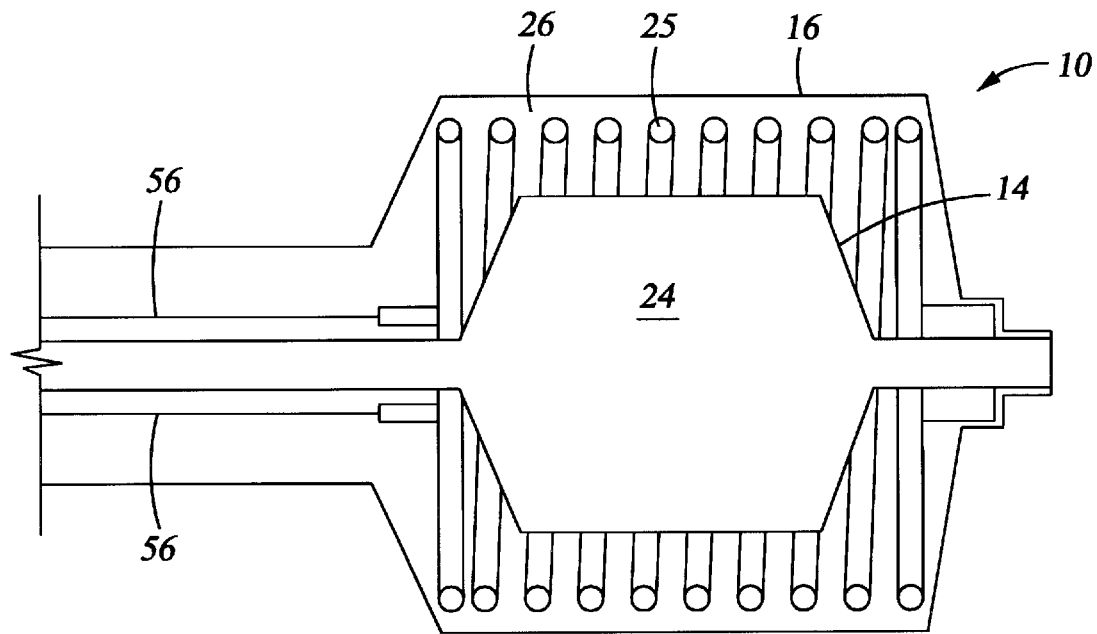
FIG. 9 is a section view of the embodiment shown in FIG. 8, in the expanded state.

FIGS. 8 and 9 show another embodiment which incorporates a self-expanding mechanism in the form of a helical spring 25. The helical spring 25 has two configurations. One configuration is shown in FIG. 8, where the length of the spring 25 is extended, and its diameter is reduced. The other configuration is shown in FIG. 9, where the length of the spring 25 is reduced, and its diameter is expanded. The distal end of the spring 25 is anchored to the distal end of the CAD 10. A spring controller 56 is attached to the proximal end of the spring 25, for transforming the spring 25 from one of these configurations to the other. Two types of spring 25 could be used.

One type of spring 25 would be biased toward the shortened configuration shown in FIG. 9, with the expanded diameter. In such a spring, it would be necessary to place the spring 25 under tension with the spring controller 56, to hold the spring 25 in the lengthened configuration, with the reduced diameter, during insertion or withdrawal of the CAD 10 through the vascular system. Then, the tension could be released to allow the spring 25 to transform to its expanded diameter to hold the housing 16 in the expanded state. With this type of spring, the spring controller 56 could be either a relatively stiff member or a cable.

Another type of spring 25 would be biased toward the lengthened configuration shown in FIG. 8, with the reduced diameter. In such a spring, it would be necessary to place the spring 25 under compression with the spring controller 56, to transform the spring 25 to the shortened configuration, with the expanded diameter, to hold the housing 16 in the expanded state. The spring 25 could be allowed to take its natural, lengthened, configuration during insertion or withdrawal of the CAD 10 through the vascular system. With this type of spring, the spring controller 56 must be a relatively stiff member.

When using a helical spring 25 as the expansion mechanism, it may be detrimental to rely entirely on the tensile or compressive strength of the housing 16 and the pumping membrane 14 to resist the force in the spring 25. For instance, with the short-biased type of spring 25, the housing 16 and the pumping membrane 14 may not have sufficient compressive strength to resist the tension placed in the spring 25 by the spring controller 56 to hold the spring in the configuration shown in FIG. 8. In such a case, the housing 16 and the pumping membrane 14 would tend to bunch up, and the spring 25 could not be transformed to its reduced diameter for passage through the vascular system. Similarly, with the long-biased type of spring 25, the housing 16 and the pumping membrane 14 may not have sufficient tensile strength to resist the compression placed in the spring 25 by the spring controller 56 to transform the spring 25 to the configuration shown in FIG. 9. In such a case, the housing 16 and the pumping membrane 14 would tend to extend axially when compression of the spring 25 is attempted, and the spring 25 could not be transformed to its expanded diameter to hold the housing 16 in the expanded state.

Figure 10:
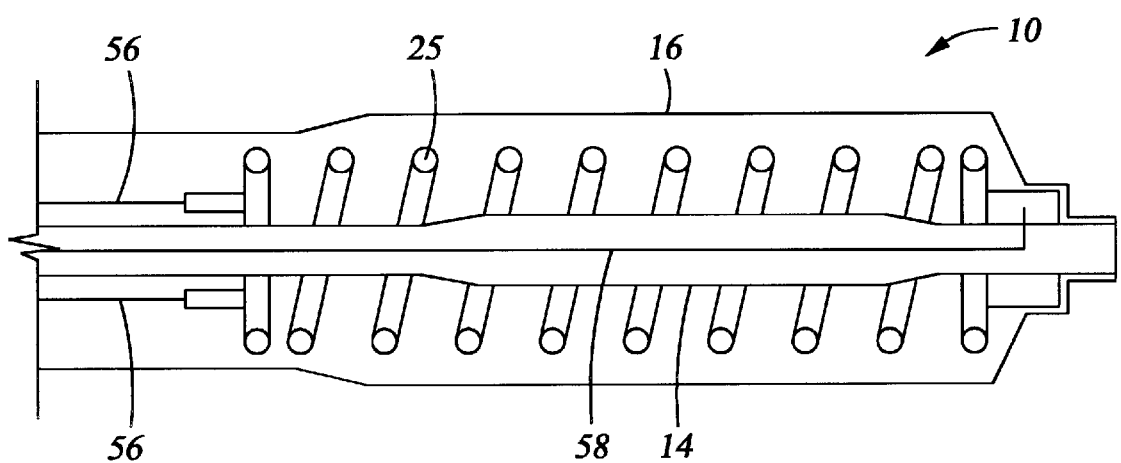
FIG. 10 is a section view of a ninth embodiment of the apparatus of the present invention, with a stiffening mandrel passing through the inner membrane, and with the membranes in the contracted state.
Figure 11:
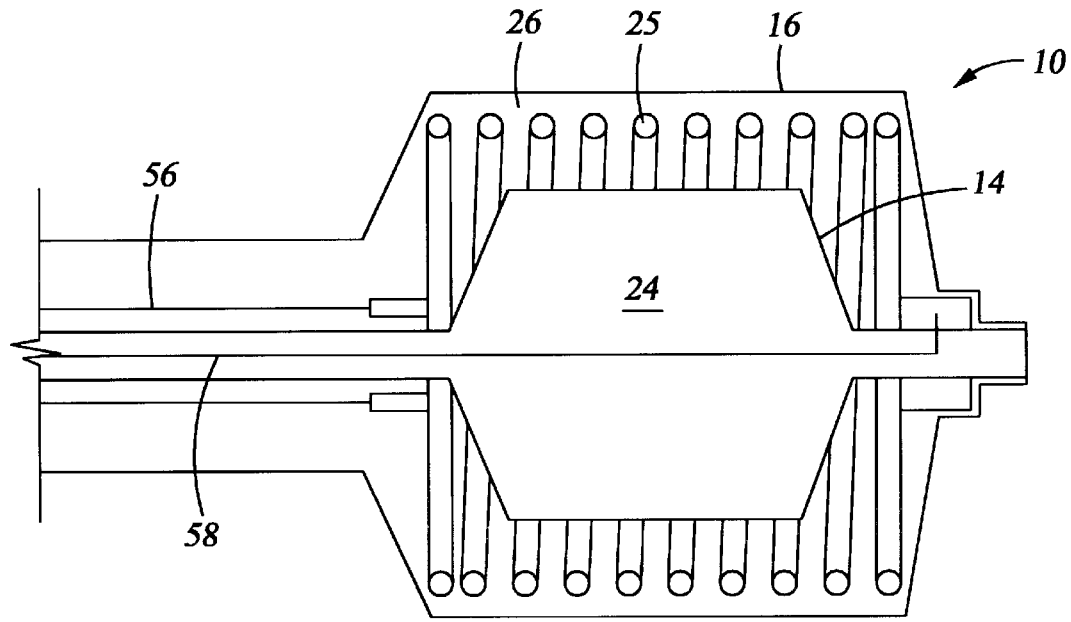
FIG. 11 is a section view of the embodiment shown in FIG. 10, in the expanded state.
Figure 12:
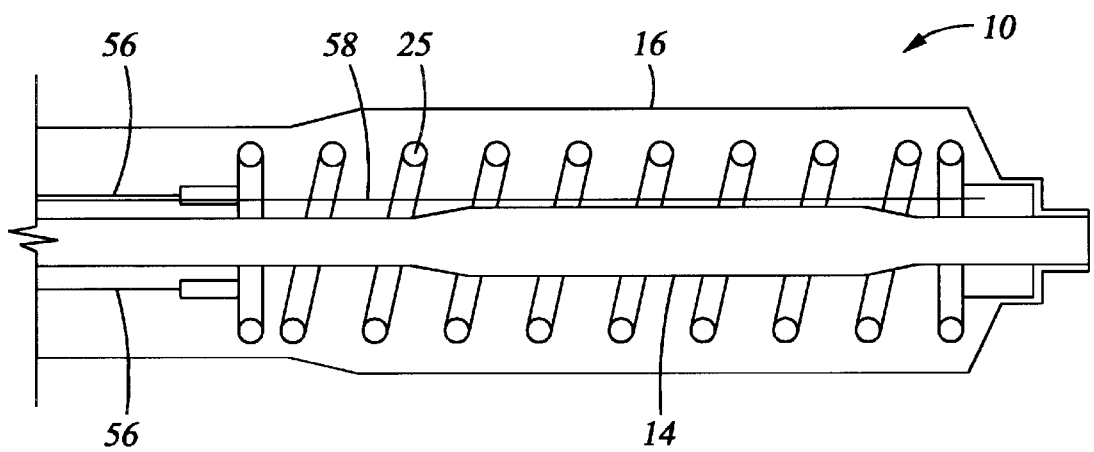
FIG. 12 is a section view of a tenth embodiment of the apparatus of the present invention, with a stiffening mandrel passing outside the inner membrane, and with the membranes in the contracted state.
Figure 13:
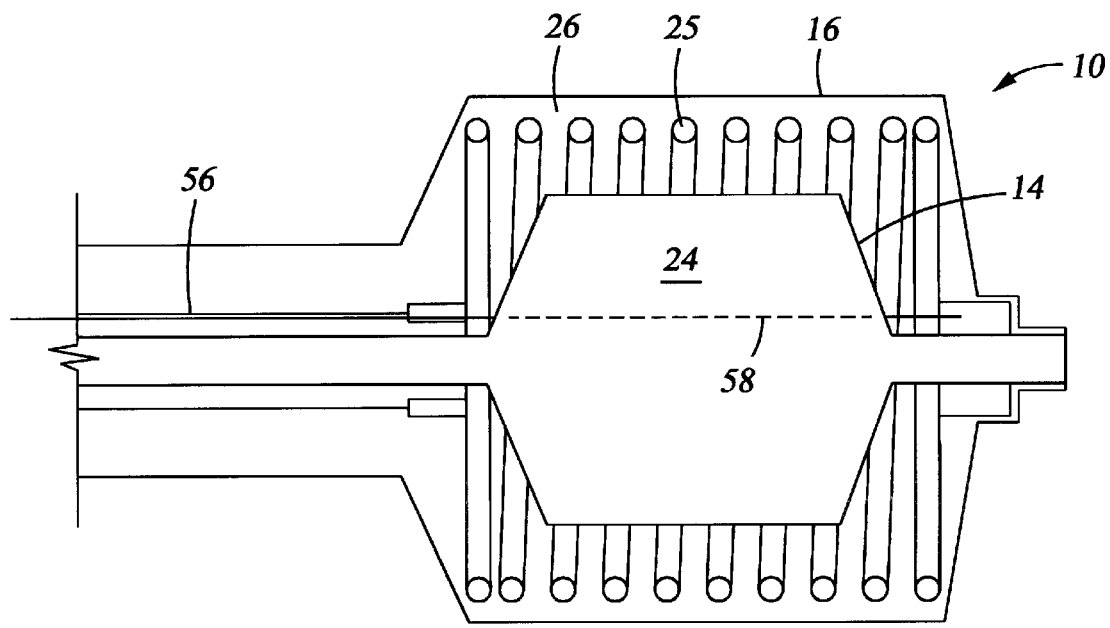
FIG. 13 is a section view of the embodiment shown in FIG. 12, in the expanded state.

The embodiments shown in FIGS. 10 through 13 can be used to alleviate this problem. FIGS. 10 and 11 show a mandrel 58 passing through the center of the pumping membrane 14, and anchored to the CAD 10 at its distal end. The penetration of the mandrel 58 through the pumping membrane 14 must be sealed. The mandrel 58 holds the distal ends of the housing 16 and the pumping membrane 14 in place during application of tension or compression by the spring controller 56. If the short-biased type of spring 25 is used, the mandrel 58 must be a relatively stiff member to resist compression. If the long-biased type of spring 25 is used, the mandrel 58 can actually be very flexible, like a wire or cable. More than one mandrel 58 can be used in each CAD 10, if required for the necessary tensile or compressive strength. FIGS. 12 and 13 show a mandrel 58 passing outside the pumping membrane 14, and inside the spring 25, and anchored to the CAD 10 at its distal end. This eliminates the necessity for penetrating the pumping membrane 14, but the pumping membrane 14 must be constructed with longitudinal folds or creases, to allow it to expand around the mandrel 58, as shown in FIG. 13.

Figure 14:
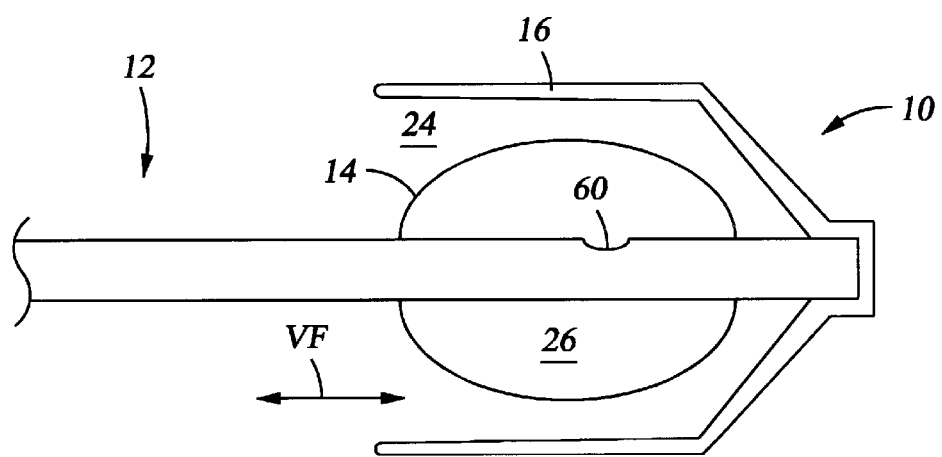
FIG. 14 is a section view of an eleventh embodiment of the apparatus of the present invention, with one variety of a non-inflatable container-type housing.

FIG. 14 shows yet another embodiment of the CAD 10, having a housing 16 and a pumping membrane 14 mounted on a catheter 12. In this embodiment, the housing 16 constitutes an open container type of enclosure, rather than an inflatable membrane type of enclosure, being open at its proximal end. The pumping membrane 14 encompasses a control chamber 26, while the space between the housing 16 and the pumping membrane 14 constitutes a pumping chamber 24 for moving vascular fluid in and out of the CAD 10, as shown by the arrow VF.

The housing 16 can be expanded to the condition shown by use of any of the previously described non-inflating mechanisms, such as the expandable stent, the expandable spring, or the expandable prongs. A control fluid port 60 is formed in the wall of the catheter 12, allowing the pressurization of the control chamber 26 with control fluid. As the control chamber 26 is pressurized with control fluid, the pumping membrane expands, forcing vascular fluid out of the pumping chamber 24. Evacuation of control fluid from the control chamber 26 collapses the pumping membrane 14, drawing vascular fluid into the pumping chamber 24.

Figure 15:
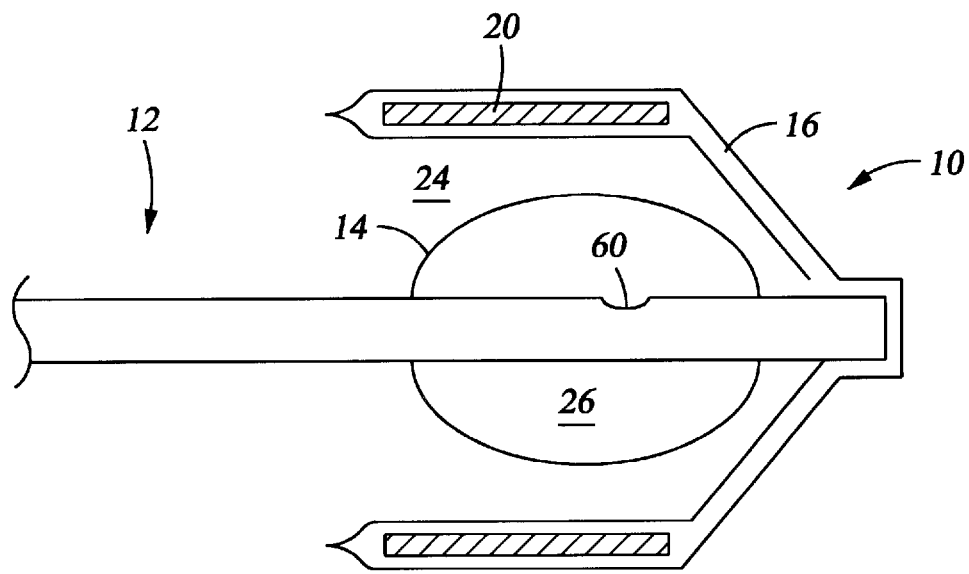
FIG. 15 is a section view of the apparatus of the present invention, showing one means of expanding the housing of the embodiment shown in FIG. 14 with a cylindrical stent.

FIG. 15 shows how a stent 20 can be imbedded within the wall of the housing 16, to hold the housing 16 in its expanded state to form a pumping enclosure for the pumping membrane 14. Regardless of what type of mechanism is used to hold the housing 16 in its expanded state, the housing gives a non-expanding enclosure which increases the pumping capacity of the CAD 10 beyond the capacity which would be available by simply expanding and contracting a pumping membrane in an expandable enclosure, such as an artery.

Figure 16:
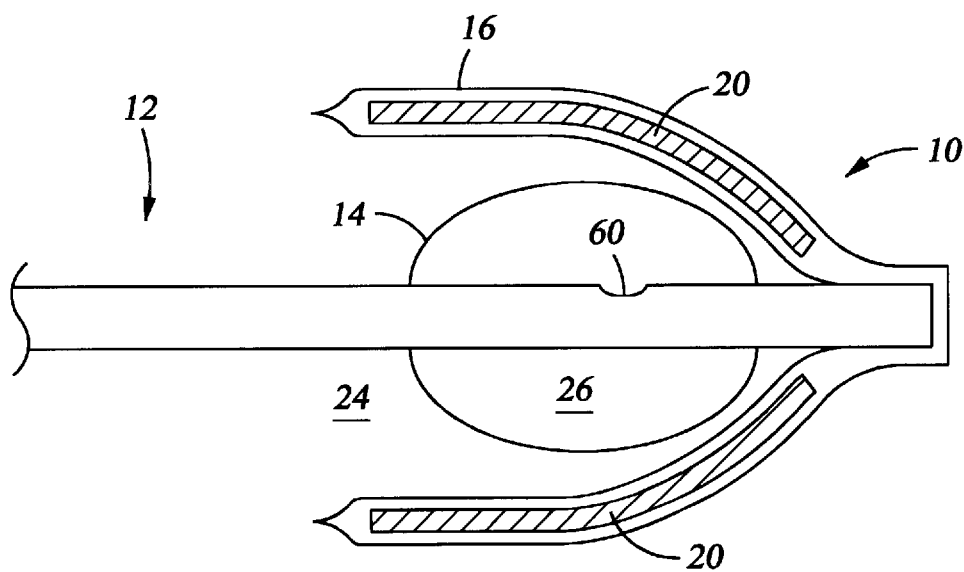
FIG. 16 is a section view of a twelfth embodiment of the apparatus of the present invention, with a second variety of non-inflatable container-type housing, and showing expansion of the housing with a tapered stent.

FIG. 16 shows another embodiment of the present invention, with a tapered stent 20 imbedded within the wall of the non-inflatable housing 16, to hold the housing 16 in its expanded state to form a pumping enclosure for the pumping membrane 14.

Figure 17:
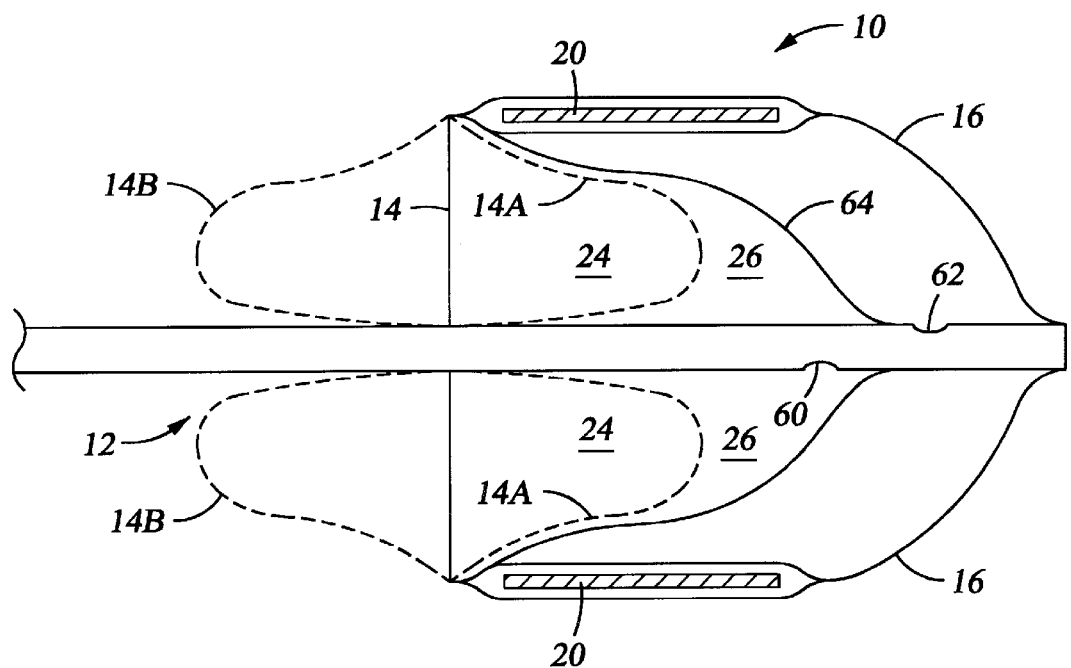
FIG. 17 is a section view of a thirteenth embodiment of the apparatus of the present invention, with one variety of inflatable membrane-type housing, and showing an inwardly and outwardly flexing pumping membrane.

FIG. 17 shows an embodiment of the CAD 10 having an inflatable housing 16, with a stent 20 imbedded in the wall of the housing 16. This embodiment also shows a flat pumping membrane 14, attached between the end of the housing 16 and the catheter 12. Rather than being flat, the pumping membrane 14 could have any other shape which allows it to flex inwardly and outwardly, as will be described. A control fluid port 60 is provided in the wall of the catheter 12, between the housing 16 and the pumping membrane 14. Further, an inflation port 62 is provided within the housing 16, and partition membrane 64 is attached to the housing 16 and the catheter 12, between the control port 60 and the inflation port 62. The catheter is constructed with multiple lumens as previously discussed, to provide control fluid to the control port 60, and to provide inflation fluid to the inflation port 62.

Pressurization of the interior of the housing 16 with inflation fluid via the inflation port 62 causes the housing 16 to expand. This creates a control chamber 26 between the partition membrane 64 and the pumping membrane 14. A pumping chamber 24 exists on the opposite side of the pumping membrane 14 from the control chamber 26. The pumping chamber 24 is shown relative to the inwardly flexed pumping membrane 14 as indicated by the dashed line 14A. The pumping membrane 14 is flexed inwardly to the approximate position indicated by the inner dashed line 14A by evacuation of the control chamber 26 via the control port 60, thereby drawing vascular fluid into the pumping chamber 24 of the CAD 10. Pressurization of the control chamber 26 with control fluid via the control port 60 causes the pumping membrane 14 to flex outwardly to the approximate vicinity of the outer dashed line 14B, thereby expelling vascular fluid from the pumping chamber 24. When the control chamber 26 is pressurized, the partition membrane 64 might tend to deflect toward the housing 16. When the control chamber 26 is evacuated, the partition membrane 64 might tend to deflect toward the pumping membrane 14.

Figure 18:
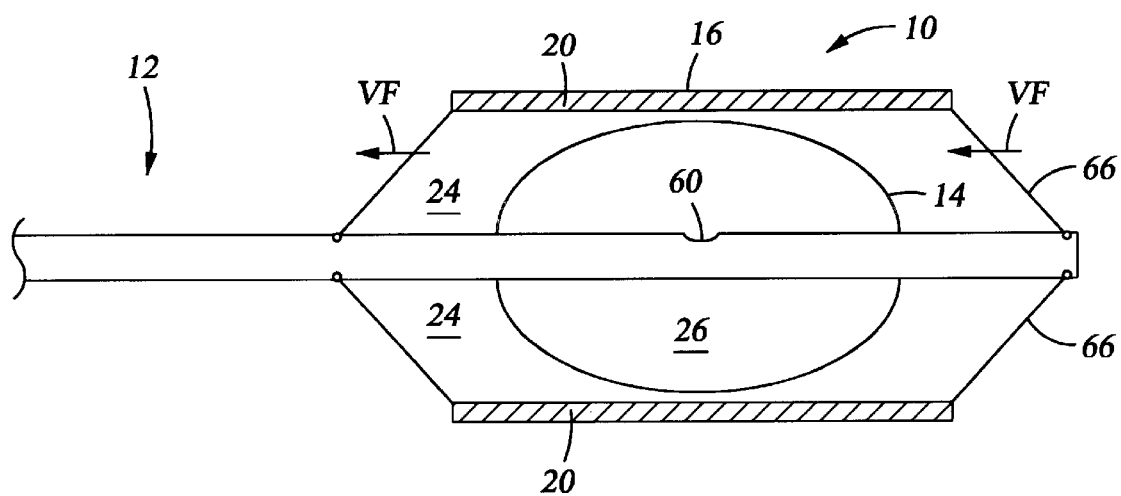
FIG. 18 is a section view of a fourteenth embodiment of the apparatus of the present invention, with a third variety of non-inflatable container-type housing having a flow-through design.

FIG. 18 shows an embodiment of the CAD 10 incorporating a flow through type of housing 16. The housing 16 of this embodiment can consist essentially of an expandable stent 20 incorporating a membrane to form a substantially tubular fluid container. Expansion of the stent 20 can be achieved by any of the non-inflatable means discussed above. Once expanded, the housing 16 will not expand further during pumping cycles, thereby providing an efficient pumping enclosure for the pumping membrane 14. The housing 16 can be tethered to the catheter 12 such as by a plurality of sutures 66 or other attachment means. The housing 16 is open on both ends, thereby allowing flow of vascular fluid through the CAD 10. Pressurization of the control chamber 26 within the pumping membrane 14 ejects vascular fluid from the pumping chamber 24. Such an embodiment would be particularly useful in the aorta, for augmentation of the aortic flow produced by the heart. The control chamber 26 would be evacuated during systole of the cardiac cycle, allowing the left ventricle to eject its load unimpeded. The control chamber 26 would be pressurized with control fluid via the control port 60 during diastole of the cardiac cycle, thereby pumping an additional load of blood through the aorta, in between systolic pulses.

Operation

The CAD 10 is arranged in its contracted, or collapsed, state, with its smallest diameter. The CAD 10 is then inserted into and through the vascular system, such as through a guide catheter, or over a wire, as is well known in the art. When the CAD 10 has been advanced to the area where circulatory assist is to be provided, the expansion mechanism, such as the stent 20, if present, is expanded along with the housing 16. This expansion can be achieved hydraulically, thermally, or by manipulation of one of the forms of selfexpanding elements. The expansion mechanism then holds the housing 16 in the expanded state to form a pumping enclosure around the pumping membrane 14. The control chamber 26 is then evacuated to move the pumping membrane 14 in a first direction and draw vascular fluid into the pumping chamber 24. Control fluid is then introduced into the control chamber 26 to move the pumping membrane 14 in a second direction and expel vascular fluid from the pumping chamber 24. Introduction and evacuation of control fluid into and from the control chamber 26 may be synchronized to the systole or diastole of the heart cycle, using the ECG signal from the patient's heart. Upon completion of pumping, the expansion mechanism is compressed, or otherwise returned to its smaller diameter, and the CAD 10 is withdrawn from the vascular system.

While the particular invention as herein shown and disclosed in detail is fully capable of obtaining the objects and providing the advantages hereinbefore stated, it is to be understood that this disclosure is merely illustrative of the presently preferred embodiments of the invention and that no limitations are intended other than as described in the appended claims.

We claim:

1. A circulatory assist device, comprising:

a catheter;

a housing attached to said catheter, said housing being selectively expandable from a first, smaller, volume to a substantially rigid state having a second, larger, volume, said housing being selectively maintainable in said expanded state;

a selectively deflectable pumping membrane attached to said catheter, said pumping membrane being disposed substantially within said housing to divide said housing into a control chamber and a pumping chamber;

a two-way control fluid flow device connected in flow communication with said control chamber, whereby selective evacuation of said control chamber with said control fluid flow device causes said pumping membrane to deflect in a first direction, and whereby selective introduction of a control fluid into said control chamber with said control fluid flow device causes said pumping membrane to deflect in a second direction; and an opening in said pumping chamber exposable to vascular fluid, whereby deflection of said pumping membrane in said first direction draws vascular fluid into said pumping chamber, and deflection of said pumping membrane in said second direction ejects vascular fluid from said pumping chamber.

2. A circulatory assist device as recited in claim 1, further comprising synchronization means for synchronizing said control fluid flow device with the heart cycle of a patient.

3. A circulatory assist device as recited in claim 1, further comprising an expansion mechanism attached to said housing.

4. A circulatory assist device as recited in claim 3, wherein said expansion mechanism is disposed within said housing.

5. A circulatory assist device as recited in claim 3, wherein:

said housing comprises an expandable wall; and said expansion mechanism is incorporated in said expandable wall.

6. A circulatory assist device as recited in claim 3, wherein said expansion mechanism comprises an expandable stent, said stent being expandable from a first relatively smaller diameter to a second relatively larger diameter.

7. A circulatory assist device as recited in claim 3, wherein said expansion mechanism comprises a self-expanding element, said self-expanding element being expandable from a first relatively smaller diameter to a second relatively larger diameter.

8. A circulatory assist device as recited in claim 1, wherein:

said pumping membrane comprises an inflatable balloon mounted on said catheter;

said control chamber is between said pumping membrane and said housing;

said pumping chamber is within said pumping membrane;

said vascular fluid opening is in said pumping membrane;

said pumping membrane collapses upon introduction of said control fluid into said control chamber; and said pumping membrane expands upon evacuation of said control fluid from said control chamber.

9. A circulatory assist device as recited in claim 1, wherein:

said pumping membrane comprises an inflatable balloon mounted on said catheter;

said control chamber is within said pumping membrane;

said pumping chamber is between said pumping membrane and said housing;

said vascular fluid opening is in said housing;

said pumping membrane expands upon introduction of said control fluid into said control chamber; and said pumping membrane collapses upon evacuation of said control fluid from said control chamber.

10. A circulatory assist device as recited in claim 1, wherein:

said pumping membrane comprises a substantially flat wall attached to said housing and to said catheter;

said control chamber is on a first side of said pumping membrane, between said pumping membrane and said housing;

said pumping chamber is on a second side of said pumping membrane opposite said first side;

said vascular fluid opening is in said housing;

said pumping membrane flexes inwardly into said housing upon evacuation of said control fluid from said control chamber; and said pumping membrane flexes outwardly from said housing upon introduction of said control fluid into said control chamber.

11. A circulatory assist device as recited in claim 1, wherein:

said pumping membrane comprises an inflatable balloon mounted on said catheter;

said housing comprises a tubular member;

said control chamber is within said pumping membrane;

said pumping chamber is between said pumping membrane and said tubular housing;

a first said vascular fluid opening is in a first end of said tubular housing;

a second said vascular fluid opening is in a second end of said tubular housing;

said pumping membrane expands upon introduction of said control fluid into said control chamber; and said pumping membrane collapses upon evacuation of said control fluid from said control chamber.

12. A method of assisting circulation of a vascular fluid, comprising:

providing a catheter mounted circulation device having a housing and a pumping membrane, with said pumping membrane dividing said housing into a control chamber and a pumping chamber;

inserting said circulation device through a vascular system of a patient, to a desired location where at least one opening of said pumping chamber is exposed to vascular fluid;

expanding said housing;

holding said housing in said expanded state;

evacuating said control chamber to deflect said pumping membrane in a first direction, thereby drawing vascular fluid into said pumping chamber; and introducing a control fluid into said control chamber to deflect said pumping membrane in a second direction, thereby expelling vascular fluid from said pumping chamber.

13. A method of assisting circulation of a vascular fluid as recited in claim 12, further comprising:

synchronizing said introducing of control fluid into said control chamber with the heart cycle of the patient; and synchronizing said evacuating of said control chamber with the heart cycle of the patient.

14. A method of assisting circulation of a vascular fluid as recited in claim 12, wherein:

said pumping membrane comprises an inflatable balloon mounted on said catheter;

said control chamber is between said pumping membrane and said housing;

said pumping chamber is within said pumping membrane;

said at least one vascular fluid flow port is in said pumping membrane;

said evacuation of said control fluid from said control chamber expands said pumping membrane, thereby drawing said vascular fluid into said pumping chamber; and said introduction of said control fluid into said control chamber collapses said pumping membrane, thereby expelling said vascular fluid from said pumping chamber.

15. A method of assisting circulation of a vascular fluid as recited in claim 12, wherein:

said pumping membrane comprises an inflatable balloon mounted on said catheter;

said pumping chamber is between said pumping membrane and said housing;

said control chamber is within said pumping membrane;

said at least one vascular fluid flow port is in said housing;

said evacuation of said control fluid from said control chamber expands said pumping membrane, thereby drawing said vascular fluid into said pumping chamber; and said introduction of said control fluid into said control chamber expands said pumping membrane, thereby expelling said vascular fluid from said pumping chamber.

16. A method of assisting circulation of a vascular fluid as recited in claim 12, wherein:

said pumping membrane comprises a substantially flat wall attached to said housing and to said catheter;

said control chamber is on a first side of said pumping membrane, between said pumping membrane and said housing;

said pumping chamber is on a second side of said pumping membrane opposite said first side;

said vascular fluid opening is in said housing;

said evacuation of said control fluid from said control chamber flexes said pumping membrane inwardly into said housing, thereby drawing said vascular fluid into said pumping chamber; and said introduction of said control fluid into said control chamber flexes said pumping membrane outwardly from said housing, thereby expelling said vascular fluid from said pumping chamber.

17. A method of assisting circulation of a vascular fluid as recited in claim 12, wherein:

said pumping membrane comprises an inflatable balloon mounted on said catheter;

said housing comprises a tubular member;

said control chamber is within said pumping membrane;

said pumping chamber is between said pumping membrane and said tubular housing;

a first said vascular fluid opening is in a first end of said tubular housing;

a second said vascular fluid opening is in a second end of said tubular housing;

said evacuation of said control fluid from said control chamber collapses said pumping membrane, thereby drawing said vascular fluid into said pumping chamber; and said introduction of said control fluid into said control chamber expands said pumping membrane, thereby expelling said vascular fluid from said pumping chamber.

* * * * *